United States Patent [19]

Ecanow et al.

[11] Patent Number: 4,558,032

[45] Date of Patent: Dec. 10, 1985

[54] SYNTHETIC WHOLE BLOOD SUBSTITUTE AND A METHOD OF MAKING THE SAME

[75] Inventors: Charles S. Ecanow, Skokie; Bernard Ecanow, Wilmette, both of Ill.

[73] Assignee: Neomed Inc., Wilmette, Ill.

[21] Appl. No.: 509,282

[22] Filed: Jun. 29, 1983

Related U.S. Application Data

[63] Continuation-in-part of Ser. No. 336,061, Dec. 31, 1981, abandoned, which is a continuation-in-part of Ser. No. 222,364, Jan. 5, 1981, Pat. No. 4,343,797, which is a continuation-in-part of Ser. No. 146,029, May 2, 1980, abandoned, which is a continuation-in-part of Ser. No. 47,071, Jun. 11, 1979, abandoned.

[51] Int. Cl.$^4$ .............................................. A61K 37/02
[52] U.S. Cl. .......................................... 514/2; 514/23
[58] Field of Search ..................... 424/177, 180; 514/2, 514/23

[56] References Cited

U.S. PATENT DOCUMENTS

| | | | |
|---|---|---|---|
| 2,591,133 | 4/1952 | Campbell et al. | 260/117 |
| 4,001,401 | 4/1977 | Bonsen et al. | 424/177 |
| 4,002,739 | 1/1977 | Turner et al. | 424/177 |
| 4,133,874 | 1/1979 | Miller et al. | 424/38 |

FOREIGN PATENT DOCUMENTS

| | | |
|---|---|---|
| 2940184 | 4/1981 | Fed. Rep. of Germany . |
| 742594 | 12/1955 | United Kingdom . |

OTHER PUBLICATIONS

Nahas et al.—Blood Substitutes and Plasma Expanders, (1978), Pub. Alan R. Liss, N.Y., pp. 259-264.
Ricketts—The Chemist and Druggist, vol. 156, (Oct. 13, 1951), pp. 495-497.
P. Lundsgaard-Hansen, M.D. and B. Tschirren, M.D., "Modified Fluid Gelatin as a Plasma Substitute", *Blood Substitutes and Plasma Expanders*, (New York: Alan R. Liss, 1978), p. 227.
Information in a letter to B. H. Gold, M.D. from H. U. Frey, M.D., Director of the Blood Transfusion Service, Central Laboratory, Berne, Switzerland, Dec. 6, 1982 and Jan. 5, 1983.
Ashwood-Smith, M. S., "Polyvinyl-Pyrolidone Solutions Used in Plasma Expander Potential Carcinogens"; *Lancet* 1, (1971), p. 1304.
De Venute, Frank and Zegna, Angelo, "Blood Exchanger with Pyridoxilated and Polymerized Hemoglobin Solution", *Surgery, Gynecology and Obstetrics*, vol. 155, (Sep. 1982), pp. 342-346.
Bucala et al, "Cytoxicity of a Perfluorocarbon Blood Substitute to Macrophages in Vitro", *Science*, vol. 220, (May 1983), pp. 965-967.
Arthur Osol, ed., *Remington's Pharmaceutical Sciences*, (Easton, Pa.: Mack Publishing Co., 1975), p. 315.
J. McMullen et al, "Pectin-Gelatin Complex Coacervates", *Journal of Pharmaceutical Science*, vol. 71, No. 6, (Jun. 1982), pp. 628-633.
Gessner G. Hawley, ed., *The Condensed Chemical Dictionary*, 9th ed., (New York: Van Nostrand Reinhold Company, 1977), p. 213.
"Blood", *Van Nostrand's Scientific Encyclopedia*, 1968, pp. 214-215.
Merck Manual, 14th ed., (Rahway, N.J.: Merck & Co., Inc., 1982).
Campbell et al.—Chem. Abst., vol. 46, (1952), p. 6797a.
Ricketts—Chem. Abst., vol. 46, (1952), p. 1215f.
Kaplan et al.—Chem. Abst. vol. 83, (1975), p. 53540w.
Vinograd-Finkel et al.—Chem. Abst. vol. 77, (1972), p. 86318j.
Chem. Abst.—8th Coll. Index, Benzimidazolin-By, pp. 5070, 5071, 5144 and 5145, (1972), and 5145s, 5146s and 5076s.
Veis et al., "Phase Separation in Polyelectrolyte Systems, I. Complex Coacervates of Gelatin", Journal of Physical Chemistry, vol. 64, (1960).

*Primary Examiner*—Sam Rosen
*Attorney, Agent, or Firm*—Ladas & Parry

[57] ABSTRACT

A composition of matter which comprises a synthetic whole blood useful as a substitute for whole natural blood and a method of making the same are disclosed. The method of manufacture yields a composition of matter comprised of a two phase coacervate system. The claimed system successfully duplicates the two phase heterogeneous physico-chemical system of naturally occurring whole blood. Also disclosed is a phase of the claimed method of manufacture which produces a composition of matter, useful as a substitute for hematocrit. Also disclosed is an embodiment employing a hemoglobin component which is preferably selected from stroma free hemoglobin, synthetic liposomes containing stroma free hemoglobin, microencapsulated stroma free hemoglobin, or emulsified droplets of coacervate containing stroma free hemoglobin. It is preferred that the microencapsulated stroma free hemoglobin when employed ranges in size from 0.1 to 10 microns. Among the main ingredients of the blood substitute composition are gelatin or modified fluid gelatin and acacia.

19 Claims, No Drawings

SYNTHETIC WHOLE BLOOD SUBSTITUTE AND A METHOD OF MAKING THE SAME

This is a continuation-in-part of our copending U.S. Ser. No. 336,061, filed Dec. 31, 1981, now abandoned, which is a continuation-in-part of our U.S. Ser. No. 222,364 filed Jan. 5, 1981, now U.S. Pat. No. 4,343,797, which is a continuation-in-part of our U.S. Ser. No. 146,029 filed May 2, 1980, now abandoned, which is a continuation-in-part of our U.S. Ser. No. 47,071 filed June 11, 1979, now abandoned.

BACKGROUND

Authorities in the fields of physiology and clinical medicine are in agreement that there is a need for an acceptable substitute for whole blood. Similar opinion exists regarding hematocrit.

In the prior art, a number of compositions, i.e.: Lactated Ringer's Solution, Dextran, Modified Gelatin, Hydroethyl Starch, Fluorocarbons and Perfluorocarbons are referred to as "blood substitutes". (Ref. Chemical Abstracts, 8th Collective Index, 1967-1971; 1972.) The scientific literature however, records no evidence that any of these compositions can function as a whole blood substitute or that they are conventionally used as such. These substances as well as albumin are employed principally to expand plasma volume, carry oxygen, or enhance oxygen transport. Whole human blood is known to possess other important capabilities and functions. Aside from intrinsic physiological limitations, the available "blood substitutes" have restricted utility by reason of known adverse reactions and incompatibilities.

With the exception of Applicants' U.S. Pat. No. 4,343,797, the prior art contains no reference to a blood substitute that has both the physico-chemical characteristics and the physiological range of whole blood. (Ref. Chemical Abstracts, 8th Collective Index, 1967-1971; 1972; Chemical Abstracts, 9th Collective Index, 1977; Chemical Abstracts, volumes, 88, 89, 90, 91, 92, 93 and 94.). Moreover, the cited prior art does not refer to a method of manufacture of such a composition. Finally, the scientific literature contains no reference to a blood substitute which like whole human blood *and* the claimed composition of matter possess both polar and non polar properties. Presently known blood substitutes are primarily either polar or non polar.

From Applicants' U.S. Pat. No. 4,343,797, it is now recognized that the physical-chemical structure of whole human blood has been successfully substantially replicated in a composition of matter known as Synthetic Whole Blood. It is now also recognized the Synthetic Whole Blood is a distinct entity fundamentally different from compositions known in the scientific literature as "blood substitutes".

Table I which follows details other fundamental differences between the claimed composition of matter and the available blood substitutes described in the prior art.

THE PHYSICOCHEMICAL STRUCTURE OF WHOLE BLOOD

From a physicochemical point of view, whole human blood in the body exists and functions as a two phase coacervate system. Erythrocytes, largely composed of water comprise the relatively non polar coacervate phase of the coacervate system referred to above. Plasma which also consists primarily of water constitutes the bulk water, relatively polar aqueous phase of the system. The two phases normally exit in equilibrium with respect to dissolved molecules and electrolytes.

Any change that significantly affects the components or their concentration of the coacervate system will disturb the normal steady state with consequent physiological effect. Thus, as one example, alteration of the electrolyte content of the plasma (i.e. change in the relatively polar water state) can result in destruction of the erythrocytes (i.e. change in the non polar coacervate phase) with consequent hemolysis.

In this invention, methods of manufacture are disclosed which produce compositions of matter that successfully duplicate the two phase physicochemical (coacervate) system of whole human blood. This duplication enables the claimed compositions to carry out virtually all of the physiological functions of whole blood, with the exception of clotting. Introduction of the claimed synthetic whole blood into the recipient does not interfere with existing clotting capability. A modification in the manufacturing process of the claimed composition will yield a composition of matter which is useful as a substitute for hematocrit.

OBJECTS

It is an object of this invention to provide an acceptable substitute for whole blood. It is another object to provide convenient methods for preparing an acceptable substitute for whole blood. It is a further object to provide a useful substitute for hematocrit and provide a convenient method for preparing the hematocrit substitute. Further objects will become self evident from the disclosure.

TABLE I

| Properties* | Lactate Ringer's Solution | Dextran | Gelatin including modified gelatin | Albumin 5% | Hydroethyl Starch | Perfluorochemicals |
|---|---|---|---|---|---|---|
| 1 | No | No | No | No | No | Yes |
| 2 | Yes | Yes | Yes | Yes | Yes | Yes |
| 3 | No | No | No | No | No | No |
| 4 | No | No | No | No | No | No |
| 5 | No | No | No | No | No | Yes |
| 6 | No | No | No | No | No | No |
| 7 | No | No | No | No | No | No |
| 8 | No | No | No | No | No | No |
| 9 | Reduction | Reduction | Reduction | Reduction | Reduction | Reduction |
| 10 | Yes | Yes | Yes | Yes | Yes | Yes |
| 11 | Does Not apply | Does Not apply | Does Not apply | Does Not apply | Does Not apply | Yes |
| 12 | No | No | No | No | No | Yes |
| 13 | Yes | Yes | Yes | Yes | Yes | Yes |

TABLE I-continued

| Properties* | Whole Human Blood | U.S. Pat. No. 4,343,797 Synthetic Whole Blood | Present Invention Synthetic Whole Blood, Gelatin and Acacia Version |
| --- | --- | --- | --- |
| 1 | Yes | Yes | Yes |
| 2 | Yes | Yes | Yes |
| 3 | Yes | Yes | Yes |
| 4 | Yes | Yes | Yes |
| 5 | Yes | Yes | Yes |
| 6 | Yes, but not equal to that of synthetic whole blood | Yes | Yes |
| 7 | No | Yes | Yes |
| 8 | Yes | Yes | Yes |
| 9 | Increase | Can be prepared to decrease or increase % | Can be prepared to decrease or increase % |
| 10 | Yes | Yes | Yes |
| 11 | Yes | No | No |
| 12 | No | Yes | Yes |
| 13 | No | Yes | Yes |

Properties*
1. Oxygen Transport
2. Carbon Dioxide Transfer
3. Oxygen can be held in reserve and released in accordance with physiological tension
4. Hemoglobin can be added or dispersed within the preparation without loss of stability
5. Transfers gasses other than $O_2$ and $CO_2$
6. Possesses both polar and non-polar properties
7. Dissolves and transports non-polar drug entities without loss of dosage-form stability
8. Transports enzyme systems without loss of stability
9. Effect on hematocrit percent after transfusion
10. Essential amino acids can be transported in stable form and desired quantity
11. Oxygen uptake ability reduced at low $O_2$ partial pressures
12. Transports physiologically useful lipid soluble entities as a stable solution
13. Universal donor characteristics

SUMMARY OF THE INVENTION

This invention comprises a composition of matter useful as a safe and effective substitute for whole, natural blood and methods of manufacture thereof. The claimed invention makes use of the concepts and process of coacervation and incorporates components which are intrinsic to whole blood. In the process of manufacture the component ingredients may be either natural or synthetic in origin. The claimed process of manufacture produces a two phase coacervate system substantially identical to the two phase physicochemical system of whole natural blood, i.e.: a non-polar coacervate phase insoluble in *and* in equilibrium with an associate polar bulk water equilibrium phase. The coacervate phase comprises from 10 to 50% of the two phase system; the bulk water equilibrium phase constitutes from 50 to 90% of the coacervate system.

The coacervate phase possess the physiological and physicochemical properties of hematocrit while the bulk water equilibrium phase is the physiological and physicochemical equivalent of blood plasma. Upon emulsification, the two phase coacervate system can be infused into a recipient and will function as whole blood. In the preferred method, however, the two phase coacervate system is brought into even closer functional equivalence with whole, natural blood during the process of manufacture, by the addition of appropriate proteins, electrolytes, a sterol, and if desired, a hemoglobin component selected from stroma free hemoglobin, synthetic liposomes containing stroma free hemoglobin, microencapsulated hemoglobin, or emulsified droplets containing stroma free hemoglobin.

As it now appears in the literature, the composition of synthetic liposomes containing stroma free hemoglobin is considered to be synthetic erythrocytes. (Reference: Miller, I. and Djordjevich, L.; U.S. Pat. No. 4,133,874 (1979). With regard to the Miller and Djordjevich reference, the possibility is mentioned that the synthetic liposomal erythrocytes that they have invented can be suspended in isotonic saline or Krebs-Ringer solution or in synthetic plasma materials and used for blood transfusion purposes. Since the vehicles given above contain large quantities of bulk water, there is a strong likelihood that oxygen uptake in such compositions is limited. This stands in direct contrast with the oxygen uptake capability of the presently disclosed invention in which microencapsulated hemoglobin and/or liposomes containing stroma free hemoglobin is incorporated in the claimed coacervate system or the coacervate phase of such a system. Both the coacervate system and the coacervate phase of the system have significant oxygen pick up. The addition of stroma free hemoglobin in other of the forms given immediately above serves significantly to enhance the oxygen uptake of these claimed compositions.

At the point that manufacture of the two phase coacervate system of the present invention is completed, the two phases may be separated. In the preferred procedure, the two component phases are separated after the additives described above have been added but before emulsification takes place.

Upon separation of the phases, the coacervate phase can be safely introduced intravenously either to carry out or to enhance the physiological functions of hematocrit. It can transport and transfer oxygen and carbon dioxide much as naturally occurring erythrocytes do. The introduced hematocrit substitute (i.e.: coacervate phase of the two phase coacervate system) will not adversely affect the percent of the recipient's hematocrit. Moreover, when it is infused, it will disperse in the blood plasma of the recipient, thereby contributing to the existing two phase physicochemical system of the naturally occurring whole blood to which it has been added. In addition, the physicochemical characteristics of the coacervate phase render it sensitive and reactive to both the physiological state and physiological changes in the recipient's blood. Finally, the claimed hematocrit substitute can readily enter and pass through the major blood vessels, capillaries and the microcirculation.

If the intended purpose is to transfuse the equivalent of whole blood, then the emulsified form of the two phase coacervate system is infused intravenously. If the preferred method is followed, the infused synthetic whole blood will be comprised of the two phase coacervate system and appropriate additives, the combination of which will have been emulsified prior to use. In its preferred form, not only can the claimed composition can carry out substantially all vital functions of naturally occurring whole blood, but in addition can be safely used in a wide variety of treatment procedures including the establishment and maintenance of extra corporeal circulation. By reason of its physicochemical characteristics, the claimed synthetic whole blood will circulate readily within the entire vascular system.

Upon transfusion, the claimed composition can establish, re-establish and/or maintain normal osmotic pressures, transport and transfer physiological gases, can carry nutrients, drug dosage forms and various physiological entities over extended perios of time without loss of stability. The transport characteristics of the claimed compositions of matter enable them to serve as a sage and reliable vehicle in hyperalimentation procedures. When it is desireable to introduce enzyme systems into the body, such systems can be added to the coacervate phase of this invention and infused through conventional intravenous methods. Enzyme systems introduched through these compositions of matter will perform their normal physiological functions.

When it is desirable to enhance the intrinsic oxygen carrying capacity of the claimed compositions, stroma free hemoglobin, synthetic liposomes containing stroma free hemoglobin, or microencapsulated hemoglobin may be added to the coacervate phase or to the emulsified coacervate system. Such addition does not affect the stability or the physiological capabilities of the claimed compositions.

The disclosed synthetic whole blood can be rendered free of foreign proteins and other elements which contribute to the adverse reactions associated with transfusion of whole human blood. Further, because this invention possess universal donor characteristics, no blood typing is necessary prior to infusion of this composition of matter. An additional important advantage of the claimed whole blood substitute over whole human blood is that it can be readily modified to meet many of the specific requirements of specific medical and surgical treatment procedures.

The guidelines which govern the quantities of the claimed synthetic whole blood that may be safely infused, are unlike those of the available blood substitutes, but are substantially identical to those that govern the use of whole human blood.

In the process of manufacture, the component ingredients may be of synthetic or natural origin. The process per se, must be carried out under aseptic conditions. Except for cooling steps that are necessary to the method of preparation, all procedures are carried out at ambient temperatures and conventional pressures. When infused, the compositions should be at a temperature that approximates 98.6° F. (37° C.).

Either of two groups of component ingredients can be used in the preparation of the claimed compositions of matter. The groups are of equal utility in producing the necessary two phase coacervate system. Irrespective of the group of ingredients selected for use, the fundamental manufacturing step remains the same; i.e. a process of coacervation constitutes the method by which the component ingredients are combined.

When the two phase coacervate system is prepared from the group of ingredients herein referred to as Group A according to U.S. Pat. No. 4,343,797, the preferred ingredients will include albumin, sodium chloride, urea, lecithin, cholesterol, and distilled water. When the coacervate system is manufactured using ingredients comprising the group referred to as Group B, the preferred ingredients will comprise acacia USP, gelatin solution or modified fluid gelatin, sterile water and 1N hydrochloric acid.

Regardless of the group of components employed to produce the two phase coacervate system, the additives used to bring the composition into closer physiological approximation with whole human blood are substantially the same. Excluding the substances used in titration and establishment of isotonicity, the additives comprise the following: cholesterol, calcium chloride, potassium chloride, electrolytes and a hemoglobin component. It is preferred, but not required that the hemoglobin component is selected from stroma free hemoglobin, synthetic liposomes containing stroma free hemoglobin, microencapsulated hemoglobin or emulsified droplets made with the coacervate phase and containing stroma free hemoglobin. Other hemoglobin components may be employed. Regardless of which of the above noted forms of the hemoglobin component forms is used, it is preferred to add it in an amount so that the final preparation will contain 1 to 20% weight to volume of stroma free hemoglobin.

Certain treatment regimens may make the addition of mucopolysaccharides, glycoproteins, proteins, enzymes and other molecules such as heparin desirable. These substances can be added to the claimed compositions and they will perform their conventional functions without altering the composition.

During the manufacture of the described coacervate system, coacervated structured, bulk water-insoluble droplets are formed. Under the conditions of the manufacture of this invention, these droplets coalesce to form the coacervate phase of the two phase coacervate system. This preparation can be readily emulsified to form droplets of any desired size. In this invention, the preferred size can range from 0.1 to 10 microns.

Except for Applicants' U.S. Pat. No. 4,343,797 the prior art contains no reference which suggests or hints at a method of manufacture of a synthetic whole blood based upon the process of coacervation; nor does it hint at or suggest the composition of a two phase coacervate system which will function virtually as whole blood. Further, the prior art makes no mention of a substitute for hematocrit comprised of the coacervate phase of the claimed coacervate system.

DETAILED DESCRIPTION

In order to explain the invention more fully, the following are descriptions of the preferred methods of preparing the claimed compositions. Specific examples of the practice of this invention are detailed in the subsequent sections of this application.

The process used to manufacture the claimed synthetic whole blood and the claimed substitute for hematocrit, using the ingredients, described in this document as comprising Group A has been detailed in applicants' U.S. Pat. No. 4,343,797 incorporated herein by reference. However, in order to present a complete description in this document, the process is briefly presented below.

Disperse from 5 to 15% weight to volume of powdered albumin in distilled water containing 0.9% weight to volume sodium chloride, 1 to 5% weight to volume urea and 0.1 to 10% weight to volume of lecithin. Store the resulting solution, undisturbed at 4° C. for 12 hours. Remove the resulting two phase coacervate system from refrigeration; then add such amount of distilled water at ambient temperature to the coacervate system as will result in a 5% weight to volume of albumin; add such quantity of NaCl to the coacervate system as will render said system isotonic with whole human blood. The coacervate system may now be separated into its two component phases, or alternatively, emulsified to produce droplets ranging in size from 0.1 to 10 microns. In its emulsified form, the composition can be used as a synthetic whole blood. The separated coacervate phase of the two phase system can be used as a substitute for hematocrit. Storage, if necessary should be at 4° to 10° C.

In the preferred method of manufacture, emulsification of the two phase coacervate system is delayed until the procedures described immediately below, are completed; add such amount of cholesterol as will result in a 1% weight to volume concentration of cholesterol in said system. Add calcium chloride powder to a concentration of 5 mg. %. Next, add potassium chloride to a concentration of 3 mg. %. The preparation is then titrated using sodium bicarbonate until a pH in the range of 7.3 to 7.45 is reached. Next, add such quantity of distilled water as will render the coacervate system isotonic with whole human blood.

Mix the preparation vigorously for 1 hour; follow the mixing step by storing the preparation at 10° C. for 148 hours. Remove the preparation from storage and emulsify it at ambient temperature to produce droplets ranging in size from 0.1 to 10 microns. The resulting composition comprises the claimed synthetic whole blood. Infusion into the recipient should be at temperatures approximating normal human temperatures. Storage if necessary should be at 4° to 10° C.

If desired, the two phases of the coacervate system may be separated by means of a separatory funnel prior to emulsification. The separated coacervate phase is useful as a substitute for hematocrit. 5 to 20% weight to volume of stroma free hemoglobin can be added to the separated coacervate phase, or prior to the emulsification step, to the two phase coacervate system containing the additive ingredients described immediately above. Addition of stroma free hemoglobin will enhance the intrinsic oxygen transport capability of both compositions of matter.

This invention also teaches a variation on the method of making a synthetic whole blood based on the ingredients of the previously referred to Group B. This method is also based on a process of coacervation. The procedure comprises the following steps: thoroughly mix 5 to 15% weight to volume of either gelatin powder or modified fluid gelatin with 5 to 15% weight to volume of acacia which has been dispersed in sterile water. The solution is then stored undisturbed at 10° C. for 24 hours, after which, it is removed from refrigeration. Ordinarily, this step will produce the required two phase coacervate system. If said system does not result, add 1N hydrochloric acid dropwise to the solution until separation of the two phases occurs, indicating formation of the coacervate system. Adjust said system to a pH in the range of 6.8 to 7.6 by adding the required amount of sodium hydroxide. If the two phase coacervate system has formed during the 24 hour period of refrigerated storage, then, as indicated above hydrochloric acid is not added; however, if the pH of said system is not in the range of 6.8 to 7.6, it is made so by adding the necessary quantity of sodium hydroxide. Following the step in which the pH is adjusted, the coacervate system is made isotonic with whole human blood by adding sterile water or sodium chloride as required. The system may then be emulsified to produce droplets ranging in size from 0.1 to 10 microns. As such, it is useful as a whole blood substitute. Alternatively, the phases are separated; the coacervate phase can be used as a substitute for hematocrit. If not infused, the compositions should be stored at from 4° to 10° C.

In the preferred method, the emulsifying step occurs after the following sequence of steps: To the two phase coacervate system described above, such amount of cholesterol is added as will result in a 1% weight to volume concentration of cholesterol in the said system. Next, add calcium chloride powder to a concentration of from 3 to 5 mg. % and potassium chloride to a concentration of 1 to 3 mg. %. The preparation is then titrated to a pH within the range of 6.8 to 7.6, preferably 7.3 to 7.5, by adding the appropriate amount of sodium hydroxide; the pH of normal whole human blood is preferred. Sterile water or sodium chloride is added as required, to render the coacervate system isotonic with whole human blood. The said system is then mixed vigorously for one hour. Following this step, the preparation is stored from 72 to 148 hours at 10° C. The preparation is then removed from refrigerated storage. After the preparation reaches ambient temperature, it is emulsified by any of the recognized methods to produce globules ranging in size from 0.1 to 10 microns. This step sufficiently completes the preparation of synthetic whole blood using the components of the previously described Group B, so that the composition can now be infused at ambient temperature into the recipient or stored at from 4° to 10° C.

If a substitute for hematocrit is to be manufactured, the two phases of the coacervative system are separated prior to emulsification by means of a separatory funnel. The coacervate phase of the system is useful as a hematocrit substitute. It can be infused at ambient temperature into a recipient or stored at from 4° to 10° C.

Stroma free hemoglobin, synthetic liposomes containing stroma free hemoglobin, microencapsulated stroma free hemoglobin, or emulsified droplets made with the coacervate phase and containing stroma free hemoglobin can be added to either the separated coacervate phase or to the two phase coacervate system, so that the final preparation will contain about 1–20% weight to volume of stroma free hemoglobin. If microencapsulated hemoglobin is used, the hemoglobin is encapsulated by the use of an appropriate coacervate system or by any of the known microencapsulation procedures. An example is given below in Example 21. The resulting microencapsulated hemoglobin component preferably ranges in size from 0.1 to 10 microns.

Such addition will enhance the intrinsic oxygen transport capability of these compositions.

Specific treatment regimes can be instrumented through the claimed synthetic whole blood; i.e. hyperalimentation, intravenous drug therapy etc. The ingredients necessary to any given treatment regime are added to the coacervate system prior to emulsification.

When the invention is prepared with the ingredients of the previously described Group A, a phospholipid is included as a desired component. Lecithin is the preferred phospholipid. Any of the following or mixtures thereof can be used in place of lecithin: cephalin, isolecithin, sphinomyelin, phosphatidyl serine, phosphatidyl inositol, phosphatidyl choline and phosphatidic acid. Other suitable compounds of the phospholipid group could be used.

Cholesterol is a desired ingredient when the preferred method of manufacture is used to make the claimed compositions of matter. However, any of the following sterols can be used in place of the preferred cholesterol: ergosterol, 7-dehydrocholesterol, $\alpha$ sitosterol, $\beta$ sitosterol, $\gamma$ sitosterol, campesterol or mixtures thereof. Other compounds of this group known to those skilled in the art may also be used.

While the above descriptions contain many specificities, these should not be construed as limitations on the scope of the invention but rather as exemplifications of preferred embodiments. Accordingly, the scope of this invention should not be determined by the described embodiments but by the appended claims and their legal equivalents.

SPECIFIC EXAMPLES

Examples of the methods by means of which the claimed compositions of matter may be manufactured follow:

EXAMPLE 1

5% weight to volume of gelatin powder (IEP: 8.2) is mixed thoroughly with 10% weight to volume of acacia which has been dispersed in sterile water. Refrigerate the solution for 12 hours at 10° C. Remove the solution from refrigeration; if the two phases of the coacervate system have not separated, add dropwise 1N hydrochloric acid until the 2 phases have separated. Adjust the solution to a pH in the range of 6.8 to 7.6, and preferably 7.3 to 7.5 by the addition of the required amount of sodium hydroxide. If the system is not isotonic with whole human blood add sodium chloride or sterile water as requried to reach isotonicity. The preparation is then emulsified to produce globules 0.1 to 10 microns in size.

EXAMPLE 2

The procedure follows Example 1 except that after the two phase coacervate system is prepared, the coacervate phase is separated from the equilibrium water phase by means of a separatory funnel. The coacervate phase can be infused intravenously and will function as hematocrit, or it may be stored at 4° to 10° C. until needed.

EXAMPLE 3

40 mls of a 5% weight to volume gelation solution (IEP: 8.2) is thoroughly mixed with 12% weight to volume of acacia dispersed in sterile water. Sterile water is added to this solution until a volume of 150 mls is reached. The solution is then stored in a refrigerator at 10° C. for 12 hours. At the end of this period, the two phase coacervate system should be formed. If this has not occurred, add 1N hydrochloric acid dropwise until the 2 phases of the system separate. By addition of sodium hydroxide adjust the pH of the system to a point in the range of 6.8 to 7.6, and preferably 7.3 to 7.5. Render said coacervate system isotonic with human blood by adding sterile water and/or sodium chloride as may be required. Following this step, add such amount of cholesterol as will result in a 1% weight to volume concentration of cholesterol in the solution; add calcium chloride powder to a concentration of 5 mg %. This step is followed by the addition of potassium chloride to a concentration of 3 mg %. Titrate the preparation to a pH in the range of 6.8 to 7.6, and preferably 7.3 to 7.5, by the addition of sodium hydroxide in the required amount. If necessary, add sodium chloride or sterile water as required to make the coacervate system isotonic with whole human blood. Next, mix the preparation vigorously for hour, then refrigerate at 10° C. for 148 hours. In this example, the end point purpose is preparation of synthetic whole blood. Accordingly, the two phase coacervate system is removed from refrigeration and emulsified at ambient temperature by means of a colloid mill to produce globules which can range in size from 0.1 to 10 microns. The emulsified composition can be infused at this point or stored at from 4° to 10° C. until needed.

EXAMPLE 4

5% weight to volume of gelatin powder (IEP: 8.2) is mixed thoroughly with 5% weight to volume of acacia which has been dispersed in sterile water. The solution is refrigerated for 24 hours at 10° C. If a two phase coacervate system is not produced by the close of the period of refrigeration, 1N hydrochloric acid is added dropwise at ambient temperature until the two phase coacervate system is produced. The remainder of the procedure follows Example 3.

EXAMPLE 5

5% weight to volume of gelatin powder (IEP: 8.2) is mixed thoroughly with 10% weight to volume of acacia which has been dispersed in sterile water. The solution is refrigerated for 24 hours at 10° C. If a two phase coacervate system is not produced by the end of the refrigeration step, add 1N hydrochloric acid at ambient temperature dropwise until the two phase coacervate system is produced. Adjust the pH of the system to a point within the range of 6.8 to 7.6, and preferably 7.3 to 7.5. Add such amount of sodium chloride or sterile water as required to make it isotonic with human blood. Emulsify the two phase coacervate system to produce droplets ranging from 0.1 to 10 microns size.

EXAMPLE 6

5% weight to volume of gelatin powder (IEP: 8.2) is mixed with 10% weight to volume of acacia dispersed in sterile water. The solution is stored for 24 hours at 10° C. The remainder of the procedure follows Example 3.

EXAMPLE 7

5% weight to volume of gelatin powder (IEP: 8.2) is mixed with 5% weight to volume of acacia which has been dispersed in sterile water. The remainder of the procedure follows Example 3 except that 10% weight to volume of stroma free hemoglobin is added to the coacervate phase prior to emulsification. This produces emulsified droplets of the final product coacervate system, containing stroma free hemoglobin. The globules of this system range in size from 0.1 to 10 microns.

EXAMPLE 8

The procedures of Example 3 are followed in their entirety except that prior to emulsification, the two phases of the prepared coacervate system are separated by means of a separatory funnel. 5% weight to volume of stroma free hemoglobin is added to the coacervate phase of the two phase system. The coacervate phase can then be used as a substitute for naturally occurring hematocrit.

EXAMPLE 9

The procedure of Example 7 is followed in its entirety except that the synthetic blood is prepared using 10% weight to volume of synthetic liposomes containing stroma free hemoglobin instead of using stroma free hemoglobin, per se.

EXAMPLE 10

The procedure of Example 3 is followed except that the synthetic blood is prepared by using emulsified droplets made with the coacervate phase and containing a quantity of stroma free hemoglobin so that the final preparation contains 1 to 20% weight to volume of stroma free hemoglobin.

EXPERIMENTS

The following are examples of in vivo administration of synthetic whole blood and the claimed substitute for hematocrit, prepared in accordance with the detailed description.

EXPERIMENT 1

From each of three common white laboratory rats, 4 cc. of blood was removed followed immediately by infusion of 4 cc. of synthetic whole blood prepared according to Example 7. This procedure was repeated after an interval of five minutes. In effect, approximately 40% of the animal's total blood volume had been removed and replaced. One rat of this series was sacrificed two hours after the experiment was completed. The lungs, heart and other tissues revealed no gross significant pathological changes. The remaining animals were sacrificed sixty hours after the second infusion of the substitute whole blood. Examination of the heart, lungs and other tissues showed no pathological changes nor any signs associated with hypoxia, pulmonary edema or adverse immunological reaction. Blood studies of all animals in this series indicated normal oxygen and carbon dioxide tensions, and normal pH values. Neither the erythrocytes nor the clotting mechanisms appeared to be adversely affected.

EXPERIMENT 2

In a second experiment, one rate received a single injection of 6 cc. of a second preparation of the substitute whole blood of Example 10 immediately following removal of 6 cc. of its blood. This animal expired approximately 70 minutes after infusion of this sample of substitute blood. Tissue studies indicated signs of intravascular disseminated coagulation. Examination and analysis of this sample of the synthetic whole blood yielded evidence of contamination and improper preparation.

EXPERIMENT 3

4 cc. of a fresh preparation of the substitute whole blood of Example 3 was administered intravenously to each of two rats in a third series without withdrawal of blood from either animal. One rat was sacrificed after 48 hours; 72 hours after infusion with substitute whole blood the second animal was sacrificed. Inspection of the tissues and red blood cells showed no pathological change or evidence of abnormal response. Clotting mechanisms appeared to be unaffected.

EXPERIMENT 4

A fourth series of tests was performed using two Nembutal anesthetized dogs. Approximately 10% of the first animal's blood was withdrawn from the femoral artery and replaced immediately with an equal quantity of substitute whole blood of Example 7. Approximately 40% of the blood volume was withdrawn from the second dog and replaced with an equal quantity of the substitute whole blood of Example 7. Samples of the circulating blood were withdrawn from each animal from the site of infusion at 3 minute intervals for 15 minutes and at 0.5 hour intervals for 2 hours thereafter. Oxygen tension measurements were determined by the IL Blood Gas Analyzer. Test results indicated an increase in $PaO_2$ levels over base line measurements. Carbon dioxide levels remained within normal limits.

Mean arterial blood pressure rose to 150/88 from 135/80 after infusion in the first animal. The mean arterial blood pressure in the second animal rose from 130/75 to 155/90, following infusion with substitute whole blood. After 24 hours, the mean arterial blood pressure stabilized at 130/70 in the first dog. Mean arterial blood pressure in the second dog stabilized at 145/75 twenty four hours after infusion. Following infusion with synthetic whole blood, mean heart rate in the first animal rose to 120 beats per minute from a base line measurement of 105. Mean heart rate following infusion of the second dog rose to 155 beats per minute from a base line reading of 110. After 24 hours the mean heart rate was measured at 98. The mean heart of the second animal stabilized after 24 hours at 99 beats per minute. Both animals were sacrificed 96 hours after infusion with substitute whole blood. Tissue studies revealed no significant evidence of pathological change or abnormal immunological reaction in the first animal. The second dog however exhibited equivocal signs of intravascular disseminated coagulation in segments of the venous system. A third dog was exposed to the same withdrawal and replacement procedures as the second animal of this series. However, the infused substitute blood in this experiment contained 10 mls of heparin. Sacrifice of this animal 96 hours after infusion and study of the organs, tissues, and red blood cells revealed no abnormal changes or signs of immunologically undesirable response.

EXPERIMENT 5

In a fifth experiment utilizing one Nembutal anesthetized dog, the infused substitute whole blood of Example 7 was prepared to include stroma free hemoglobin. Approximately 40% of the blood volume of this animal was withdrawn and replaced with the preparation described immediately above. Mean blood pressure after infusion rose to 150/90 from a baseline measurement of 135/80; after 24 hours, the mean blood pressure stabilized at 140/85. Following infusion with substitute whole blood mean heart rate rose from 110 to 145 beats per minute. After 24 hours, the mean heart rate was measured at 105. PaO$_2$ levels remained increased over base line measurements for approximately 95 minutes. Upon restoration of base line PaO$_2$ levels, intermittent administration of oxygen from an external source resulted in elevated oxygen tensions in this animal that persisted for approximately 6½ hours. This result suggests that the claimed composition remains in the circulation, retaining its ability to transport oxygen efficiently for an appreciable period of time.

EXPERIMENT 6

A sixth study involved the withdrawal of 6 cc. of blood from each of two common white laboratory rats and the immediate replacement with an equal amount of synthetic whole blood made in the method of Example 3. Blood studies indicated elevated oxygen tensions, normal carbon dioxide levels and normal pH values. Both animals were sacrificed 72 hours after infusion of the synthetic whole blood. Inspection of lungs, heart and other tissues revealed no significant sign of pathological change or adverse immunological response.

EXPERIMENT 7

The seventh experiment involved the withdrawal of 4 cc. of blood from each of 2 common white laboratory rats, followed by the immediate replacement of 4 cc. of the composition made in accordance with the method of Example 8, (Substitute for hematocrit). Blood studies indicated elevated oxygen tensions, normal carbon dioxide levels and nor pH values. Both animals were sacrificed 48 hours after infusion of the hematocrit substitute. Inspection of the lungs, heart and other tissues disclosed no sifnificant evidence of pathological change or adverse immunological reaction.

The following Examples 11–20 recited below, relate to the embodiment employing microencapsulated hemoglobin, or emulsified droplets.

EXAMPLE 11

The procedure of Example 7 is followed in its entirety except that the synthetic blood is prepared using microencapsulated stroma free hemoglobin or emulsified droplets made with the coacervate phase and containing stroma free hemoglobin, instead of using stroma free hemoglobin.

EXAMPLE 12

The procedure of Example 8 is followed in its entirety except that the synthetic blood is prepared using microencapsulated stroma free hemoglobin or emulsified droplets made with the coacervate phase and containing stroma free hemoglobin, instead of using stroma free hemoglobin.

EXAMPLE 13

40 mls of a 5% weight to volume gelatin solution (IEP: 8.2) is thoroughly mixed with 12% weight to volume of acacia dispersed in sterile water. Sterile water is added to this solution until a volume of 150 mls is reached. The solution is then stored in a refrigerator at 10° C. for twelve hours. At the end of this period, the two phase coacervate system should be formed. If this has not occurred, add 1N hydrochloric acid dropwise until the two phases of the system separate. By addition of sodium hydroxide adjust the pH of the system to a point in the range of 6.8 to 7.6, and preferably 7.3 to 7.5. Render the said coacervate system isotonic with human blood by adding sterile water and/or sodium chloride as may be required. Following this step, add such amount of cholesterol as will result in a 1% weight to volume concentration of cholesterol in the solution; add calcium chloride powder to a concentration of 5 mg %. This step is followed by the addition of potassium chloride to a concentration of 3 mg %. Titrate the preparation to a pH in the range of 6.8 to 7.6, preferably 7.3 to 7.5, by the addition of sodium hydroxide in the required amount. If necessary, add sodium chloride or sterile water as required to make the coacervate sysem isotonic with whole human blood. Next, add 5–15% weight to volume of emulsified droplets made with the coacervate phase and containing stroma free hemoglobin, and then mix the preparation vigorously for 1 hour. Then refrigerate at 10° C. for 148 hours. In this example, the end point purpose is preparation of synthetic whole blood. Accordingly, the two phase coacervate system is removed from refrigeration and emulsified at ambient temperature by means of a colloid mill to produce globules which can range in size from 0.1 to 10 microns. The emulsified composition can be infused at this point or stored at from 4° to 10° C. until needed.

EXAMPLE 14

5% weight to volume of modified fluid gelatin (IEP: 8.2) is mixed thoroughly with 10% weight to volume of acacia which has been dispersed in sterile water. Refrigerate the solution for 12 hours at 10° C. Remove the solution from refrigeration; if the two phases of the coacervate system have not separated, add dropwise 1N hydrochloric acid until the two phases have separated. Adjust the solution to a pH in the range of 6.8–7.6, preferably 7.3 to 7.5, by the addition of the required amount of sodium hydroxide. If the system is not isotonic with whole human blood and sodium chloride or sterile water as required to reach isotonicity. The rest of the procedure follows that of Example 13.

EXAMPLE 15

The procedure follows Example 14 except that after the two phase coacervate system is prepared, the coacervate phase is separated from the equilibrium water phase by means of a separatory funnel, and 10 to 15% weight to volume of emulsified droplets made with the coacervate phase and containing stroma free hemoglobin, is added to the coacervate phase which can then be infused intravenously and will function as hematocrit, or it may be stored at 4° to 10° C. until needed.

EXAMPLE 16

5% weight to volume of gelatin powder (IEP: 8.2) is mixed thoroughly with 5% weight to volume of acacia which has been dispersed in sterile water. The solution is refrigerated for 24 hours at 10° C. If a two phase coacervate system is not produced by the close of the period of refrigeration, 1N hydrochloric acid is added dropwise at ambient temperature until the two phase coacervate system is produced. The remainder of the procedure follows Example 13.

EXAMPLE 17

5% weight to volume of modified fluid gelatin (IEP 8.2) is mixed thoroughly with 10% weight to volume of acacia which has been dispersed in sterile water. The solution is refrigerated for 24 hours at 10° C. If a two phase coacervate system is not produced by the end of the refrigeration step, add 1N hydrochloric acid at ambient temperature dropwise until the two phase coacervate system is produced. Adjust the pH of the system to a point within the range of 6.8 to 7.6, preferably 7.3 to 7.5. Add such amount of sodium chloride or sterile water as required to make it isotonic with human blood. Emulsify the two phase coacervate system to produce droplets ranging from 0.1 to 10 microns size.

EXAMPLE 18

5% weight to volume of gelatin powder (IEP: 8.2) is mixed with 10% weight to volume of acacia dispersed in sterile water. The solution is stored for 24 hours at 10° C. The remainder of the procedure follows Example 13.

EXAMPLE 19

5% weight to volume of gelatin powder (IEP: 8.2) is mixed with 5% weight to volume of acacia which has been dispersed in sterile water. The remainder of the procedure follows Example 16 except that 5% weight to volume of microencapsulated stroma free hemoglobin is added prior to emulsification.

EXAMPLE 20

The procedures of Example 13 are followed in their entirety except that prior to emulsification, the two phases of the prepared coacervate system are separated by means of a separatory funnel. 5% weight to volume of microencapsulated stroma free hemoglobin is added to the coacervate phase of the two phase system. The coacervate phase can then be used as a substitute for naturally occurring hematocrit.

EXPERIMENTS

The following are examples of in vivo administration of synthetic whole blood and the claimed substitute for hematocrit, prepared in accordance with the Examples 13–20.

EXPERIMENT 8

From each of 3 common white laboratory rats, 4 cc. of blood was removed followed immediately by infusion of 4 cc. of synthetic whole blood prepared according to Example 13. This procedure was repeated after an interval of five minutes. In effect, approximately 40% of the animal's total blood volume had been removed and replaced. One rat of this series was sacrificed 2 hours after the experiment was completed. The lungs, heart and other tissues revealed no gross significant pathological changes. The remaining animals were sacrificed 60 hours after the second infusion of the substitute whole blood. Examination of the heart, lungs and other tissues showed no pathological changes nor any signs associated with hypoxia, pulmonary edema or adverse immunological reaction. Blood studies of all animals in this series indicated normal oxygen and carbon dioxide tensions, and normal pH values. Neither the erythrocytes nor the clotting mechanisms appeared to be adversely affected.

EXPERIMENT 9

In the next experiment, one rat received a single injection of 4 cc. of a second preparation of the substitute whole blood of Example 15 immediately following removal of 4 cc. of its blood. This animal expired approximately 70 minutes after infusion of this sample of substitute blood. Tissue studies indicated signs of intravascular disseminated coagulation. Examination and analysis of this sample of the synthetic whole blood yielded evidence of contamination and improper preparation.

EXPERIMENT 10

4 cc. of a fresh preparation of the substitute whole blood of Example 15 was administered intravenously to each of 2 rats in a third series without withdrawal of blood from either animal. One rat was sacrificed after 48 hours; 72 hours after infusion with substitute whole blood the second animal was sacrificed. Inspection of the tissues and red blood cells showed no pathological change or evidence of abnormal response. Clotting mechanisms appeared to be unaffected.

EXPERIMENT 11

Another series of tests was performed using 2 Nembutal anesthetized dogs. Approximately 10% of the first animal's blood was withdrawn from the femoral artery, and replaced immediately with an equal quantity of substitute whole blood of Example 11. Approximatley 40% of the blood volume was withdrawn from the second dog and replaced with an equal quantity of substitue whole blood of Example 11. Samples of the circulating blood were withdrawn from each animal from the site of infusion at the 3 minute intervals for 15 minutes and at 0.5 hour intervals for 2 hours thereafter. Oxygen tension measurements were determined by the IL Blood Gas Analyzer. Test results indicated an increase in $PaO_2$ levels over base line measurements. Carbon dioxide levels remained within normal limits.

Mean arterial blood pressure rose to 150/88 from 135/80 after infusion in the first animal. The mean arterial blood pressure in the second animal rose from 130/75 to 155/90, following infusion with substitute whole blood. After 24 hours, the mean arterial blood pressure stabilized at 130/70 in the first dog. Mean arterial blood pressure in the second dog stabilized at 145/75, 24 hours after infusion. Following infusion with synthetic whole blood, mean heart rate in the first animal rose to 120 beats per minute from a base line measurement of 105. Mean heart rate following infusion of the second dog rose to 155 beats per minute from a base line reading of 110. After 24 hours the mean heart rate was measured at 98. The mean heart of the second animal stabilized after 24 hours at 99 beats per minute. Both animals were sacrificed 96 hours after infusion with substitute whole blood. Tissue studies revealed no significant evidence of pathological change or abnormal immunological reaction in the first animal. The second dog however exhibited equivocal signs of intravascular disseminated coagulation in segments of the venous system. A third dog was exposed to the same withdrawal and replacement procedures as the second animal of this series. However, the infused substitute blood in this experiment contained 10 mls of heparin. Sacrifice of this animal 96 hours after infusion and study of the organs, tissues, and red blood cells revealed no abnormal changes or signs of immunologically undesireable response.

EXPERIMENT 12

In another experiment utilizing one Nembutal anesthetized dog, the infused substitute whole blood of Example 12 was used. Approximately 40% of the blood volume of this animal was withdrawn and replaced with the preparation described immediately above. Mean blood pressure after infusion rose to 150/90 from a base line measurement of 135/80; after 24 hours, the mean blood pressure stabilized at 140/85. Following infusion with substitute whole blood mean heart rate rose from 110 to 145 beats per minute. After 24 hours, the mean heart rate was measured at 105. $PaO_2$ levels, intermittent administration of oxygen from an external source resulted in elevated oxygen tensions in this animal that persisted for approximately 6½ hours. This result suggests that the claimed composition remains in the circulation, retaining its ability to transport oxygen efficiently for an appreciable period of time.

EXPERIMENT 13

Another study involved the withdrawal of 6 cc. of blood from each of 2 common white laboratory rats and the immediate replacement with an equal amount of synthetic whole blood made in the method of Example 12. Blood studies indicated elevated oxygen tensions, normal carbon dioxide levels and normal pH values. Both animals were sacrificed 72 hours after infusion of the synthetic whole blood. Inspection of lungs, heart and other tissues revealed no significant sign of pathological change or adverse immunological response.

EXPERIMENT 14

Another experiment involved the withdrawal of 4 cc. of blood from each of 2 common white laboratory rats, followed by the immediate replacement of 4 cc. of the composition made in accordance with the method of Example 20, (Substitute for hematocrit). Blood studies indicated elevated oxygen tensions, normal carbon dioxide levels and normal pH values. Both animals were sacrificed 48 hours after infusion of the hematocrit subsitute. Inspection of the lungs, heart and other tissues disclosed no significant evidence of pathological change or adverse immunological reaction.

EXAMPLE 21

This is the procedure explaining how to prepare and employ microencapsulated stroma free hemoglobin. With respect to the above Examples, this procedure occurs *after* the coacervate system has been formed, the phases are separated, and 1 to 20% stroma free hemoglobin component has been added to the lower coacervate layer. The lower coacervate layer containing the stroma free hemoglobin is combined with the equilibrium liquid water layer and emulsified so that the final emulsion contains particles (droplets) which can range from 0.1 to 10 microns in size. Next, 1 to 5% formaldehyde solution is added dropwise to the emulsified preparation until the desired degree of shell structuring of the droplets is achieved. The degree of structuring can range from semi-solid or gel-like to rigid, and is achieved either through the amount of formaldehyde added or through the length of the period of storage. After the desired degree of structuring is achieved, the preparation is stored anywhere between 5 to 40 hours at 20° to 40° C. On removal from storage, the preparation will have separated into two layers, the bottom one of which contains microencapsulated globules substantially spherical in shape, containing stroma free hemoglobin. The upper layer consists of equilibrium liquid water. The two layers are separated by means of a separatory funnel or other acceptable means. The microencapsulated spheres are washed with the equilibrium liquid water, until substantially all traces of formaldehyde are completely removed. The microencapsulated spheres containing stroma free hemoglobin can then be dispersed in physiological saline solution, in the coacervate phase of any of the herein described coacervate systems, or added to the coacervate phase of the two phase coacervate system. After this step, the composition is then emulsified. The resultant emulsion is prepared so that the droplets can range in size from 0.1 to 10 microns. When the microencapsulated spheres containing stroma free hemoglobin are incorporated into the two phase coacervate system as described above, the result of the procedure is microencapsulated globules containing stroma free hemoglobin incorporated in droplets of the coacervate phase which in turn is suspended in the equilibrium liquid water phase.

In practice, where optimal sustained oxygen uptake and release is desired, minimal structuring of the microencapsulated spheres is preferred. Depending upon the physiological effect to be achieved, differing proportions of microencapsulated spheres of differing degrees of shell hardness can be combined. This will result in special release effects which can be used when introducing drugs, nutrients, enzyme systems. In other words, the composition can be so prepared as to give the desired specific rate of release of any of the components contained within the microencapsulated spheres. The procedure to incorporate drugs, nutrients, enzyme systems, et cetera, into synthetic blood containing microencapsulated stroma free hemoglobin is the same as the procedure herein described to incorporate drugs, nutrients enzyme systems, et cetera, into synthetic blood containing microencapsulated hemoglobin.

Conclusion

A synthetic whole blood useful as a substitute for natural whole blood and a composition useful as a substitute for hematocrit are disclosed as are the methods of making these compositions. The synthetic whole blood is comprised of a two phase coacervate system with physicochemical and physiological properties that are very similar to those of whole natural blood. The hematocrit substitute is comprised of the coacervate phase of the two phase coacervate system.

In manufacturing the synthetic whole blood, ingredients such as electrolytes, stroma free hemoglobin, synthetic liposomes containing stroma free hemoglobin, microencapsulated stroma free hemoglobin, emulsified droplets made with the coacervate phase and containing stroma free hemoglobin, and an appropriate sterol can be incorporated. If desired, the synthetic whole blood can be used to introduce enzymes, nutriments and drug dosage forms into the recipient's circulation.

Animal experiments have demonstrated that this invention can be used as a substitute for natural whole blood and further, that the coacervate phase of the disclosed coacervate systems can be safely and effectively used as a substitute for hematocrit.

What we claim is:

1. A method of preparing a synthetic whole blood substitute which comprises the steps of:
    (a) mixing thoroughly 5 to 15% weight to volume of a gelatin selected from modified fluid gelatin or gelatin powder with 5 to 15% weight to volume of acacia which has been dispersed in sterile water;
    (b) storing the solution undisturbed at a temperature of from about 4° to 10° C. for 12 to 72 hours to produce a two phase coacervate system comprising an aqueous coacervate phase and a bulk water phase;

(c) adjusting the pH of said system within the range of whole human blood by the addition of an alkaline substance; and (d) adding such amount of a salt to said system as will make it isotonic with whole human blood.

2. The method of claim 1 including the additional steps of: adding hydrochloric acid dropwise to the solution at ambient temperature to enhance formation of the two phase coacervate system, adjusting the pH of said system with NaOH, and adding NaCl to render said system isotonic with whole human blood.

3. A composition of matter useful as a substitute for whole blood which is prepared according to the method of claim 1.

4. The method of claim 1 comprising the additional step of separating the two phase coacervate system into its aqueous coacervate phase and its equilibrium bulk water phase.

5. A composition of matter consisting of the coacervate phase of a two phase coacervate system prepared according to the method of claim 4 which is useful as a semi-prepared synthetic substitute for naturally occurring hematocrit.

6. The method of claim 4 which comprises the additional step of adding a hemoglobin component selected from stroma free hemoglobin, synthetic liposomes containing stroma free hemoglobin, or microencapsulated stroma free hemoglobin, or emulsified droplets made with the coacervate phase and containing stroma free hemoglobin, to the said coacervate phase, so that the final product contains 1 to 20% weight to volume of said hemoglobin component.

7. The method of claim 1 which comprises the additional step of adding such amount of a sterol as will result in a 1% weight to volume of a sterol in the two phase coacervate system.

8. The method of claim 7 wherein the sterol is selected from a group consisting of cholesterol, ergosterol, 7-dehydrocholesterol, α sitosterol, β sitosterol, γ-sitosterol, campesterol and mixtures thereof.

9. The method of claim 8 wherein the sterol is cholesterol.

10. The method of claim 9 which comprises the additional step of adding calcium chloride powder to a concentration of 5 mg %.

11. The method of claim 10 which comprises the additional step of adding potassium chloride to a concentration of 3 mg %.

12. The method of claim 11 which comprises the additional step of titrating said coacervate system to pH in the range of about 7.3 to 7.5, by adding an alkaline substance.

13. The method of claim 1, including the step of emulsifying the two phase coacervate system to produce droplets ranging in size from about 0.1 to about 10 microns.

14. The method of claim 1 which comprises the additional step of adding another component selected from enzymes, proteins, or drugs.

15. A synthetic whole blood substitute comprising an aqueous solution of about 5 to 15% weight to volume acacia, about 5 to 15% weight to volume of a gelatin selected from modified fluid gelatin or gelatin powder; an alkaline substance sufficient to adjust the pH to that of whole human blood; and an amount of a salt sufficient to render the solution isotonic with whole human blood; said components forming a coacervate system having a coacervate phase and an equilibrium bulk water phase.

16. The synthetic whole blood substitute according to claim 15, including a sterol, $CaCl_2$, KCl, enzymes, proteins, drugs, a hemoglobin component selected from stroma free hemoglobin, synthetic liposomes containing stroma free hemoglobin, microencapsulated hemoglobin, or emulsified droplets made with the coacervate phase and containing stroma free hemoglobin, or mixtures thereof.

17. The coacervate phase of the synthetic whole blood substitute of claim 15, said coacervate phase comprising a semi-prepared synthetic substitute for hematocrit.

18. The synthetic whole blood substitute of claim 16, wherein the sterol is selected from cholesterol, ergosterol, 7-dehydrocholesterol, α sitosterol, β sitosterol, γ sitosterol, campesterol, or mixtures thereof.

19. The synthetic whole blood substitute of claim 15, in the form of an emulsion having droplets from 0.1 to 10 microns in size.

* * * * *